United States Patent [19]
Lieber et al.

[11] Patent Number: 5,873,837
[45] Date of Patent: Feb. 23, 1999

[54] SYSTEM AND METHOD FOR REMOTE MEASUREMENT OF FLUID FLOW

[76] Inventors: Claude P. Lieber, 1514 Monticello Dr., Gladwyne, Pa. 19035; Rajeev Bhatia, 201 Wayne St., Narberth, Pa. 19072

[21] Appl. No.: 929,228

[22] Filed: Sep. 9, 1997

[51] Int. Cl.⁶ ............................................ A61B 5/02
[52] U.S. Cl. ................................... 600/504; 600/500
[58] Field of Search ................... 600/500–506; 128/897–898

[56] References Cited

U.S. PATENT DOCUMENTS

| | | | |
|---|---|---|---|
| 4,349,034 | 9/1982 | Ramsey, III | 600/494 |
| 4,402,310 | 9/1983 | Kimura | 128/4 |
| 4,787,395 | 11/1988 | Yanashima et al. | 128/661 |
| 4,793,358 | 12/1988 | Kimura et al. | 128/654 |
| 4,881,413 | 11/1989 | Georgi et al. | 600/504 |
| 5,072,736 | 12/1991 | Ogawa et al. | 128/680 |
| 5,170,792 | 12/1992 | Sturgill et al. | 128/661 |
| 5,188,112 | 2/1993 | Sturgill et al. | 128/661 |
| 5,230,341 | 7/1993 | Polaschegg | 128/668 |
| 5,267,569 | 12/1993 | Lienhard | 128/691 |
| 5,279,302 | 1/1994 | Tamano | 128/661 |
| 5,279,303 | 1/1994 | Kawamura et al. | 600/496 |
| 5,325,728 | 7/1994 | Zimmerman et al. | 600/504 |
| 5,360,005 | 11/1994 | Wilk | 600/504 |
| 5,439,003 | 8/1995 | Schnurer et al. | 600/505 |
| 5,450,758 | 9/1995 | Smoll | 600/504 |
| 5,494,043 | 2/1996 | O'Sullivan et al. | 600/500 |
| 5,507,291 | 4/1996 | Stribl et al. | 600/504 |
| 5,520,178 | 5/1996 | Dahn et al. | 128/637 |
| 5,531,714 | 7/1996 | Dahn et al. | 604/264 |
| 5,595,182 | 1/1997 | Krivitski | 128/692 |
| 5,615,683 | 4/1997 | Toge et al. | 128/666 |

*Primary Examiner*—Cary E. O'Connor
*Assistant Examiner*—Michael Astorino

[57] ABSTRACT

System and method for remote measurement of flow through an expansible conduit, particularly a surgically implanted arteriovenous or arterioarterial prosthetic.

4 Claims, 8 Drawing Sheets

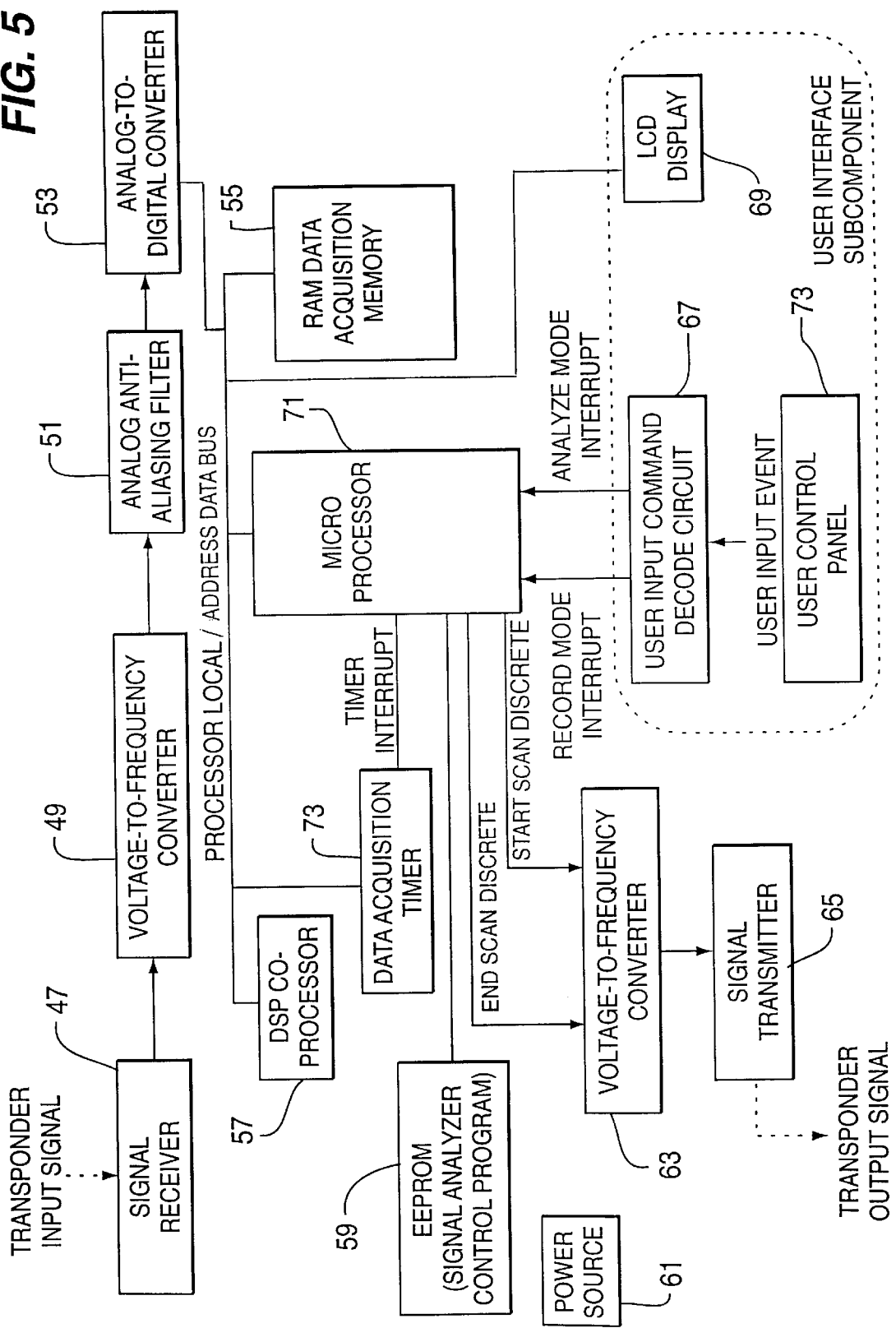

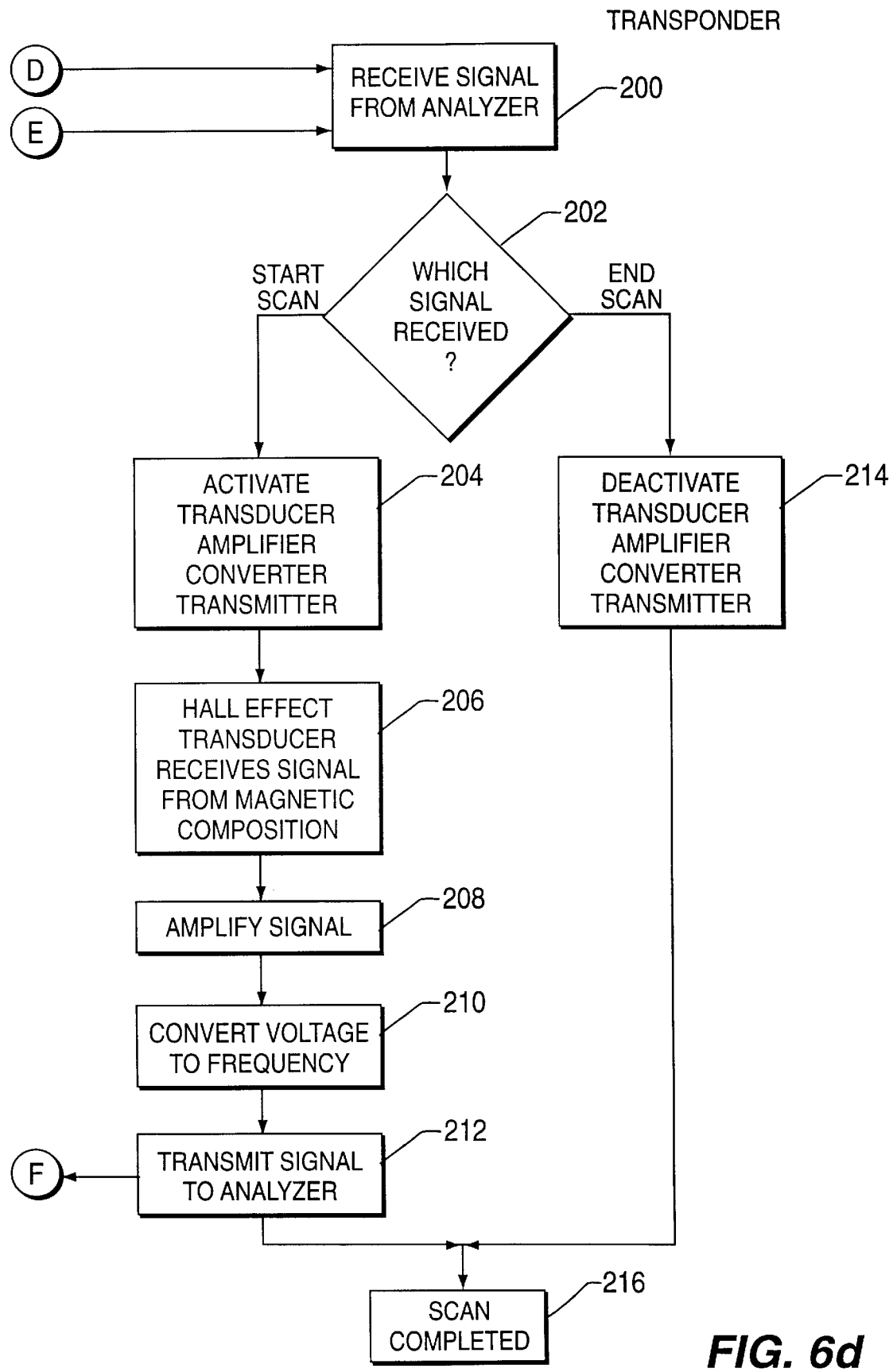

SYSTEM AND METHOD FOR REMOTE MEASUREMENT OF FLUID FLOW

BACKGROUND OF THE INVENTION

The present invention generally relates to a system for measuring fluid flow through a conduit. The present invention relates more specifically to measuring blood flow and most specifically to measuring blood flow through surgically implanted prosthetics.

Surgically implanted synthetic vascular prosthetics are used to replace diseased arteries and veins and to permit hemodialysis. However, the useful lifetime of such prosthetics can be limited by the formation of clots within them or by endothelial hyperplasia. Extensive clotting may constrict blood flow sufficiently to cause other medical incidents, such as loss of limb or dialysis access.

Methods currently exist for monitoring a prosthetic in order to obtain advance warning of constricted blood flow. Most commonly, the patient visits an out-patient facility and ultrasonographic measurements are performed to determine flow or the extent of clotting. It would be preferable, however, if the monitoring could be done in a physician's office or dialysis suite, using a small, affordable electronic instrument. It would also be advantageous if the examination could be done by medical support personnel, such as a nurse or technician, without the need for extensive technical training.

SUMMARY OF THE INVENTION

The invention is a system for monitoring fluid flow in an expansible conduit. To accomplish this goal, the preferred system comprises, in addition to the expansible conduit, a magnetic composition, a transponder that responds to magnetic flux from the magnetic composition by emitting a wireless signal, and a signal analyzer.

The wireless signal (also referred to simply as a "signal") is an electromagnetic signal, preferably one that is frequency-modulated. The analyzer receives and stores the digitized voltage analog of the signal, calculates the peak-to-peak amplitude and frequency profiles of a baseline and currently acquired signals, thereby providing a means of objectively characterizing fluid flow. Results of the flow analysis are displayed on an LCD display along with a graphical display of the baseline and currently acquired signals.

The invention includes a related method for monitoring fluid flow through an expansible conduit. The preferred method comprises three steps. In step one, over a first period of time, a voltage (either amplified or unamplified) caused by the flow is measured. That step generates a first waveform of voltage (or current) versus time. In a subsequent step, over a second period of time, a voltage caused by flow is again measured as a function of time, and a second waveform showing voltage versus time is generated. In a third step, the difference between the first and second waveforms, as regards their amplitudes or frequencies, is calculated.

BRIEF DESCRIPTION OF THE DRAWINGS

FIG. 5. is a system level block diagram of the signal analyzer of FIG. 1.

DESCRIPTION OF THE PREFERRED EMBODIMENTS

Figure 1:
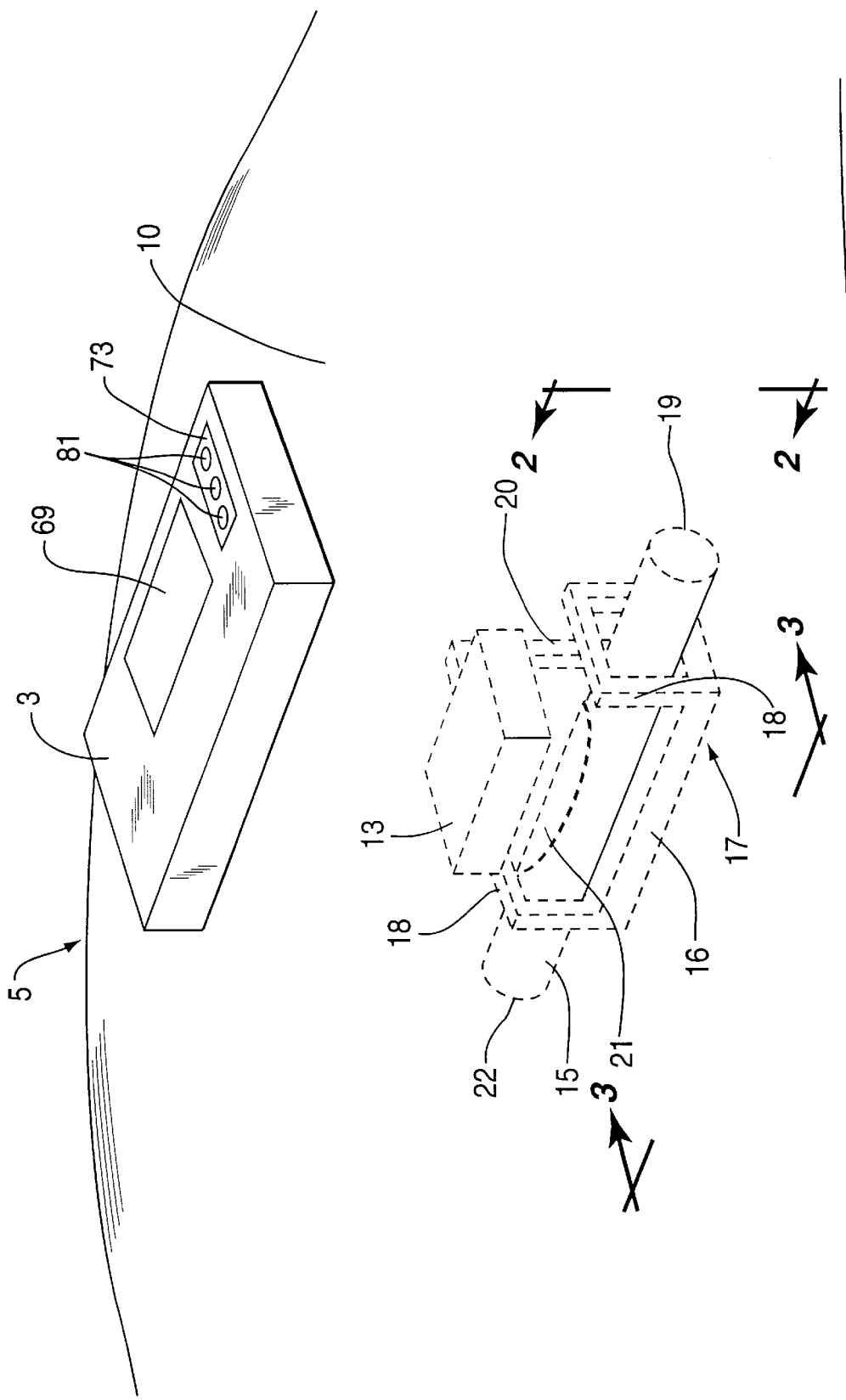
FIG. 1. is a schematic drawing showing a perspective view of a system with a transponder and an arteriovenous or arterioarterial synthetic prosthetic in a limb partially cut away for illustrative purposes.
Figure 2:
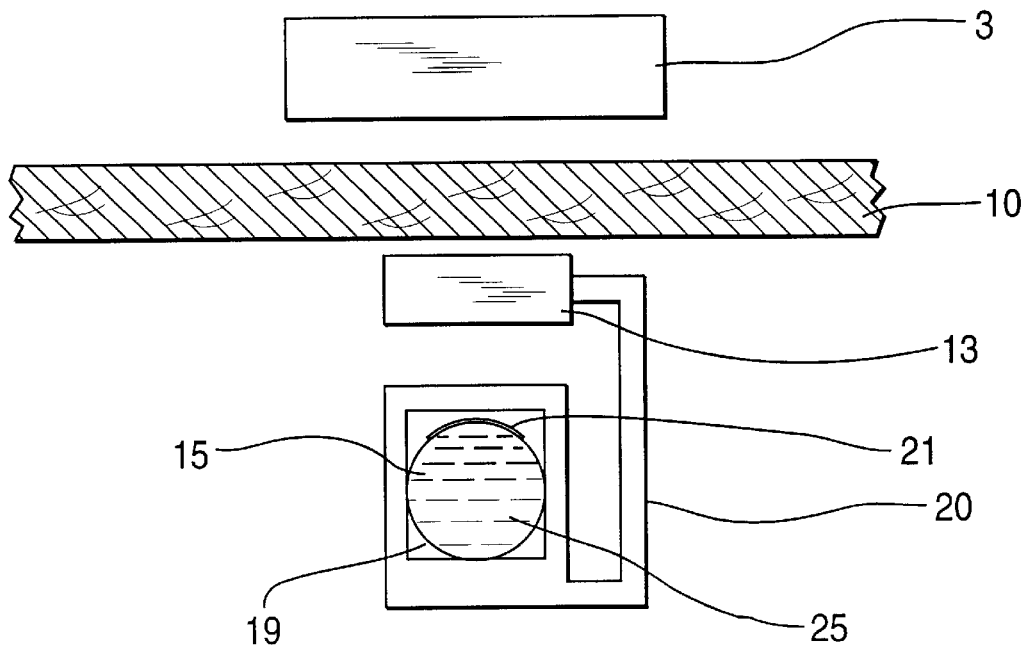
FIG. 2. is a front elevational view along 2—2 of FIG. 1.
Figure 3:
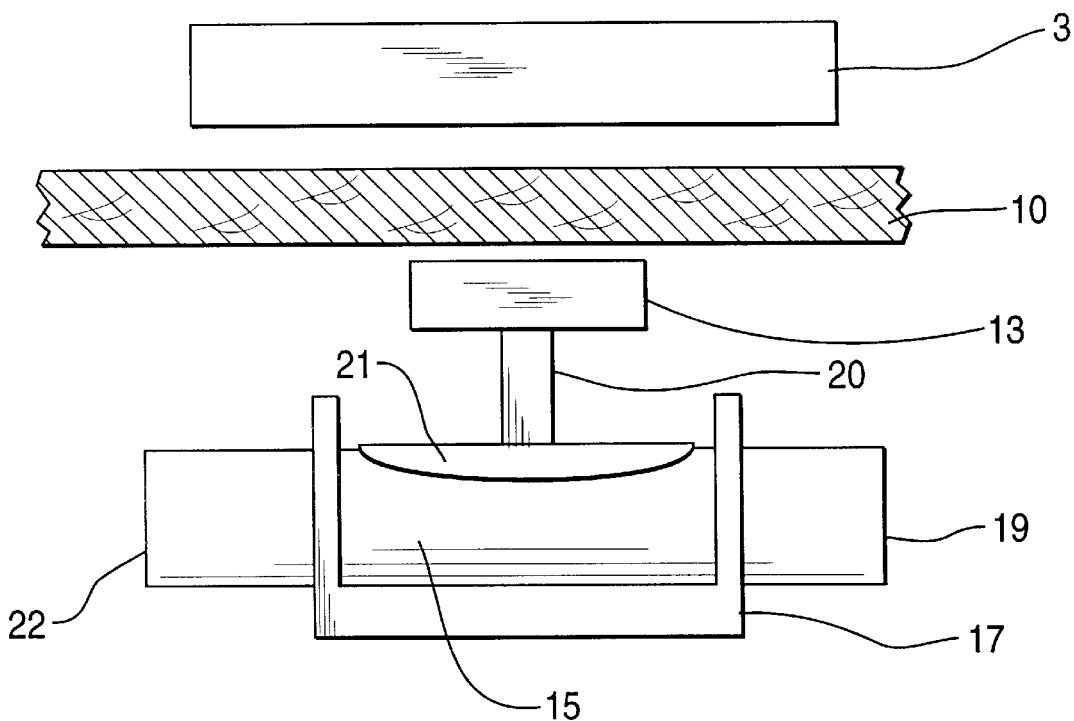
FIG. 3. is a side elevational view along 3—3 of FIG. 1.

FIG. 1–3 provide a schematic overview of the system set up to monitor blood flow through an arteriovenous or arterioarterial prosthetic 15 that is an expansible conduit located inside a limb 5. Because the limb is for 5 illustrative purposes, no attempt is made to represent an actual limb.

As shown in FIG. 1, a transponder 13 is affixed to the prosthetic 15 for purposes of detecting voltage fluctuations created by a magnetic composition 21 that coats part of the surface of the prosthetic. The transponder 13 converts the flux of magnetic composition 21 to a voltage and transmits an information signal to a remote signal analyzer 3 that is outside the limb. The signal analyzer has a control panel 73 with buttons 81 that allow the user to control the operation of the analyzer and transponder. The analyzer also contains a display panel 69. In FIG. 1, the barrier 10 between transponder 13 and analyzer 3 is the skin/peritoneum barrier 10.

The system allows a user holding the analyzer 3 to obtain information about fluid flow through the prosthetic. In most cases, the signal analyzer 3 will be used in the same room as the person with the implanted prosthetic.

FIG. 1–3 also show the positioning of the transponder 13 near the flexible conduit 15 as accomplished by a non-conductive housing 17 (preferably plastic) that comprises a base 16, two end pieces 18 connected to opposite ends of the base, and an arm 20 that connects the transponder 13 to the base 16. The prosthetic 15 fits through the openings of the two end pieces and, except for the fact that it expands or contracts as the blood pressure increases or decreases, is prevented by the end pieces from moving relative to the transponder. The prosthetic 15 may be bound to the end pieces 18 by a non-toxic chemical bonding agent. An area on the outer surface of the prosthetic is coated with a magnetic particle-epoxy composition 21.

In FIG. 2, the blood 25, shown as dashed lines, fills the conduit 15. The free ends (19, 22) of the prosthetic 15,in actual use, are grafted to the two ends of an artery or a vein (not shown) so that there is continuous pulsatile blood flow through the prosthetic.

Figure 4:
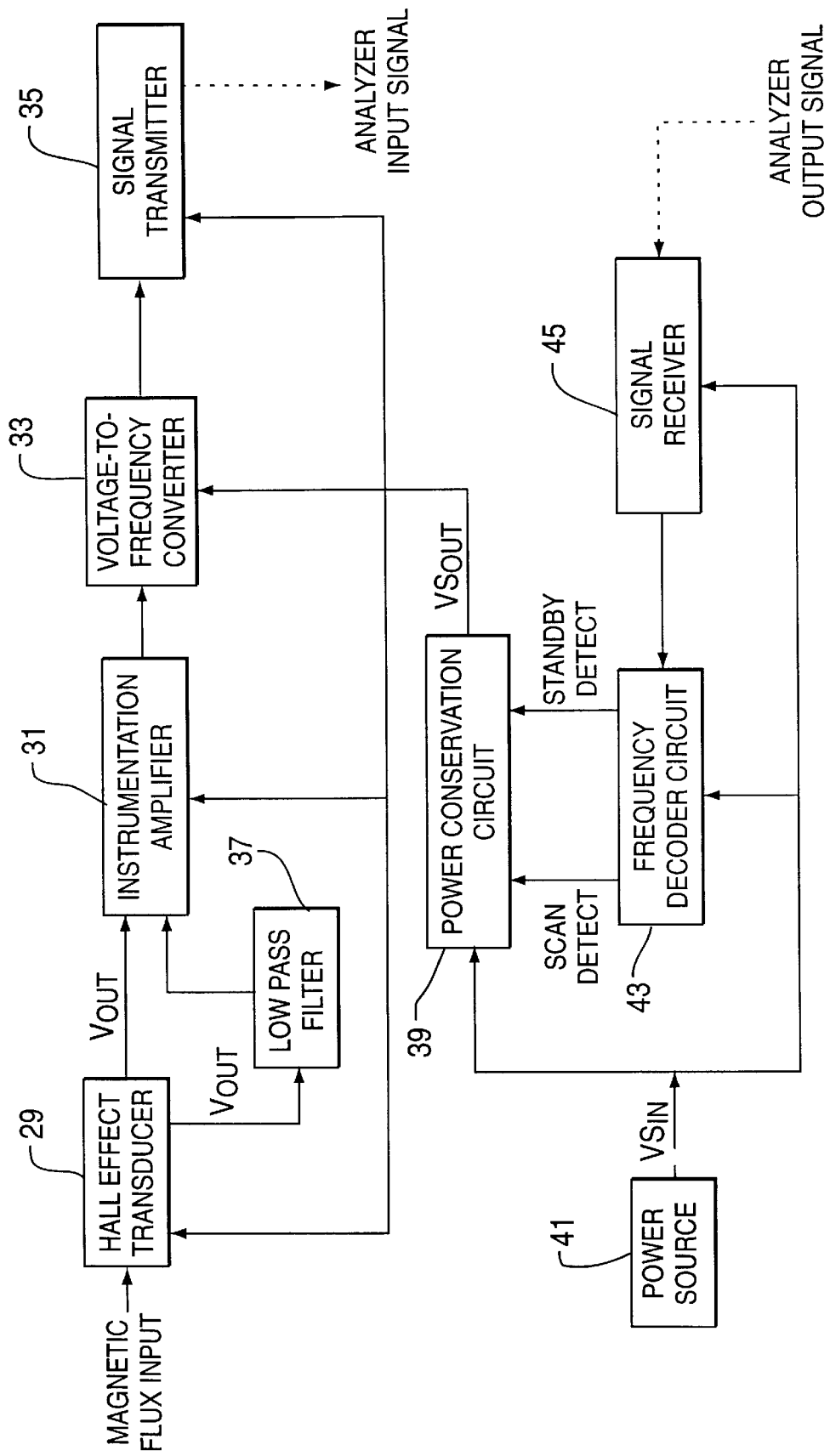
FIG. 4. is a system level block diagram of the transponder of FIG. 1.

A system level block diagram of the preferred transponder 13 is provided in FIG. 4. The transponder 13 preferably comprises the following elements identified in FIG. 4: a Hall Effect transducer 29, an amplifier 31, a low pass filter 37, a voltage-to-frequency converter 33, a signal transmitter 35, a power control circuit, and a power source 41 (for example, +/−9 V DC) to power the transponder. The power control circuit preferably comprises a signal receiver 45, a frequency decoder circuit 43 and a power conservation circuit 39.

The relationship between the components of the transducer 13 can, with reference to FIG. 4, be described as follows: the Hall Effect transducer 29 upon detecting a magnetic flux sends one voltage signal to the instrumentation amplifier 31 and another voltage signal via the low pass filter 37 to the instrumentation amplifier 31. The low pass filter transmits only slowly oscillating signals (for example, those less than 100 HZ) or nonoscillating signals to the amplifier. As a result, the amplifier 31 amplifies the difference between the two input voltages, automatically subtracting undesired constant background offset voltage. The instrumentation amplifier 31 transmits the amplified voltage signal to the voltage-to-frequency converter 33 which in turn passes a signal to the signal transmitter 35 for transmission to the signal analyzer 3. Power for the transducer comes from power source 41, and is controlled by a power conservation circuit 39 that, via a frequency decoder circuit 43 and a signal receiver 45, responds to scan and standby signals received from the signal analyzer 3. The power conservation circuit 39 responds to a scan signal, the scan mode, by powering the Hall Effect transducer, instrumentation amplifier, voltage to frequency converter, and signal transmitter and to the standby signal, the standby mode, by deactivating the Hall Effect transducer 29 and signal transmitter 35. The distance between the magnetic composition 21 and the transponder 13 is adjusted so that there is a linear relationship between that distance and the Hall Effect voltage. An acceptable distance is believed to range up to 1 mm and preferably between 0.5 and 1 mm.

Increasing pressure exerted by the blood on the wall of the conduit 15 causes a radial expansion of the conduit, a decrease in the distance from the magnetic composition 21 to a Hall Effect transducer 29 in the transponder 13, an increase in the magnetic flux seen by the transducer, and an associated increase in the resulting output voltage of that transducer. The changes in the pressure, flux, and voltage over time are wave-like in nature, and mirror the wave-like, pulsatile nature of the blood flow. The result is a displacement waveform.

As noted previously, the transponder 13 has scan and standby modes of operation. The signal analyzer 3 has three modes of operation: standby, record, and analyze. Both the record and analyze modes of the signal analyzer 3 trigger the transponder 13 to enter its scan mode and then, at an appropriate time interval, to enter its standby mode. The analyzer 3 is in standby mode at power up when the analyzer 3 is neither in the record nor analyze mode.

A system level block diagram of the signal analyzer 3 is provided in FIG. 5. The preferred signal analyzer in FIG. 5 comprises: a power source 61, a signal receiver 47, a frequency-to-voltage converter 49, an analog anti-aliasing filter 51, an analog-to-digital converter 53 (e.g. a 16-bit converter), a microprocessor 71, a signal analyzer control program 59, a data acquisition timer 73, a DSP coprocessor 57, and RAM data acquisition memory (e.g., 64K×32) 55, a voltage-to-frequency converter 63, a signal transmitter 65, a display means (such as an LCD display or a paper printer) 69, a user input command decode circuit 67, and a user control panel 73. Panel 73 includes desired controls that allow the user to instruct the signal analyzer 3 as to which mode it should enter and what type of information (examples include an actual waveform or a constriction alert) should be displayed by the display means. The ultimate design of control panel 73 will depend upon the application of the invention. The controls are generally identified as elements 81 in FIG. 1.

The interrelationship of the components of the signal analyzer 3 will be discussed with reference to FIG. 5. The signal analyzer is powered by a power source 61. From control panel 73, the user can control whether the signal analyzer is in standby mode or whether it should be in record mode or analyze mode; also whether it should display a waveform, a constriction alert or other alert, or display information on the status of the power source of the analyzer. Upon input from the user, the control panel 73 transmits a signal to the user input command decode circuit 67, which circuit sends a signal to the microprocessor 71 to initiate the requested record mode or analyze mode. A signal analyzer control program 59 in EEPROM (electrically erasable programmable read-only memory) directs the microprocessor 71, in conjunction with the data acquisition timer 73, the DSP coprocessor 57, and the RAM data acquisition memory 55, to carry out the appropriate mode function (record or analyze). At appropriate times during the record and analyze modes, the microprocessor sends a signal to the voltage-to-frequency converter 63, where it is converted to a "start scan" signal for transmission by the signal transmitter 65 to the transponder 13. When the transponder completes its scan mode, it sends a signal that is received by the receiver 47 of the analyzer. The received signal is transmitted in the signal analyzer 3 to its frequency-to-voltage converter 49, then to its analog anti-aliasing filter 51, whose function is to prevent frequency components greater than the highest frequency of interest in the signal from distorting the frequency analysis performed by the signal analyzer, and then to its analog-to-digital converter 53. Alternatively, the frequency-to-voltage converter 49, the anti-aliasing filter 51, and the analog-to-digital converter 53 can be eliminated from the signal analyzer and their functions performed by the microprocessor 71.

The analog-to-digital converter 53 provides a signal for processing by the microprocessor 71, (under the direction of the analyzer control program 59) in conjunction with the data acquisition timer 73, DSP coprocessor 57, and RAM data acquisition memory 55. The signal contains information about the amplitude and frequency of the waveform acquired by the transponder during its scan mode. If the analyzer is in analyze mode, it will compare the waveform to a previous stored waveform as to amplitude and/or frequency and display a result of that comparison on the LCD display panel 69.

The signal analyzer receives from the transponder, over a period of time (for example, 1 second) that is controlled by the data acquisition timer 73 and set by the analyzer control program 59, a signal containing information about the displacement waveform acquired by the transponder. Then the data acquisition timer interrupts the control program, upon which the program causes the signal analyzer to send an "end scan" signal to the transponder, which signal places the transponder in standby mode. The signal analyzer converts the signal received from the transponder into a digitized voltage waveform, and stores the amplitude and frequency data for subsequent comparison and display. If, for example, the rate of the displacement waveform is 100 Hz, the Nyquist sampling rate is 200 Hz minimally. The peak-to-peak amplitude swing of a displacement waveform (several periods of which can be acquired in one second) is obtained by averaging over several periods in the same scan mode run to minimize physiological variances and stored for subsequent comparison.

The analyze mode of the signal analyzer combines the data acquisition feature of the record mode with a data analysis feature. In the latter, the signal analyzer compares the displacement wave forms obtained in the analyze mode and a prior record mode. If the peak-to-peak amplitudes differ by 3 dB or more, the display will display a "constriction alert" indicating that the constriction has reached a dangerous level.

In analyze mode, in addition to peak-to-peak assessment of the displacement waveform, the control program will instruct the DSP co-processor to calculate the power spectral density of the averaged displacement waveform. Frequency information provided by the power spectral density is used to further characterize the constriction as being in-flow or out-flow in nature.

Figure 6A:
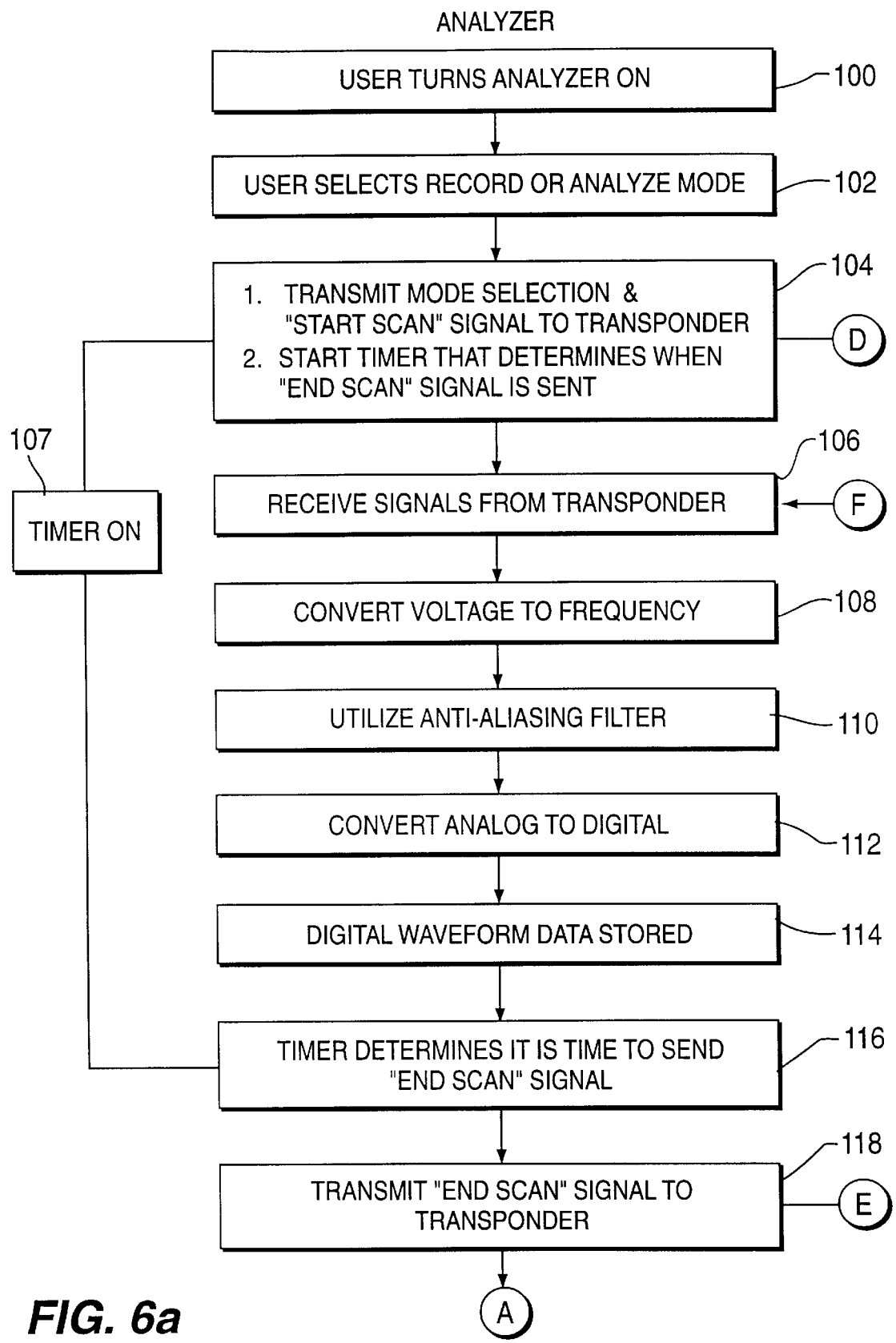
FIG. 6 a–d. are operational flow diagrams for a preferred system.
Figure 6B:
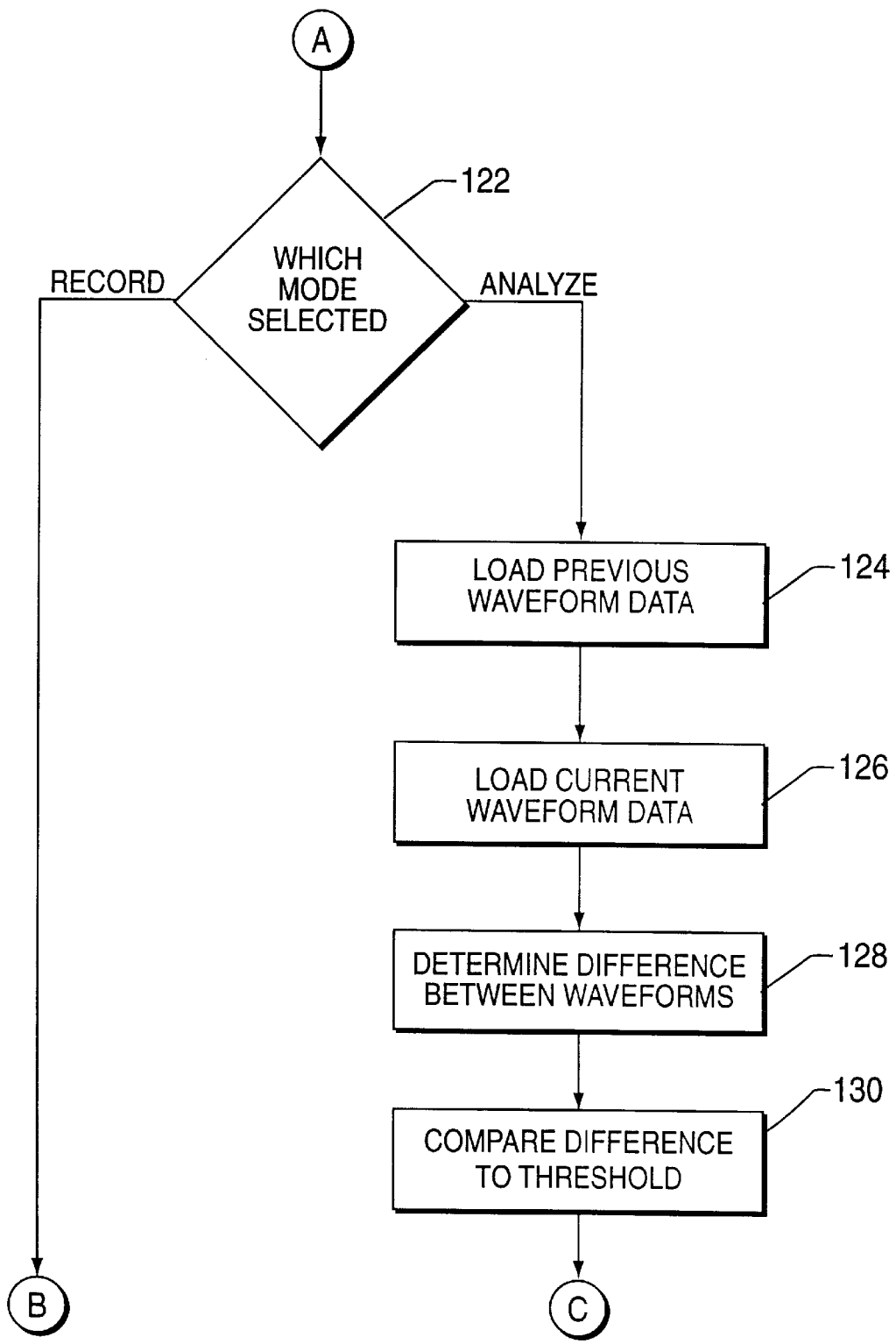
Figure 6C:
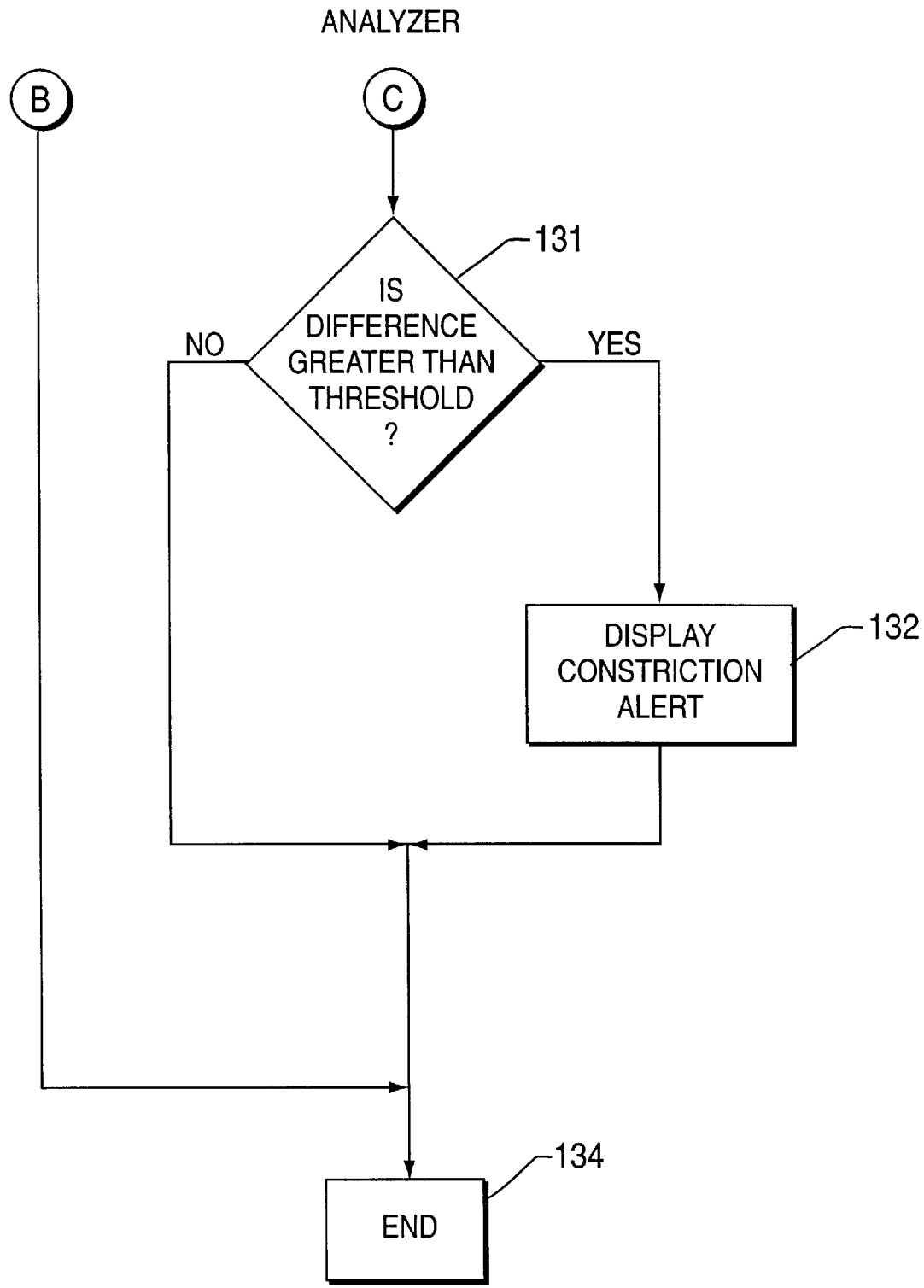

The invention can also be under stood by referring to the flow diagram in FIG. 6: The user turns the analyzer on at 100 and then selects either the record mode (for a first period of time) or the analyze mode (for a second period of time) at 102. In response, the analyzer at 104 transmits a "start scan" signal to the transponder and starts the data acquisition timer that determines when the "end scan" signal will be sent. While the timer is on, the analyzer receives voltage signals from the transponder at 106 and converts those voltage signals to frequency signals at 108. The timer utilizes its anti-aliasing filter at 110 and converts the resulting analog signal to a digital signal at 112. The digital data, which represents a digital waveform, is stored at 114. The steps at 106, 108, 110, 112 and 114 continue until the data acquisition timer determines that it is time to send an "end scan" signal at 116. The analyzer transmits an end scan signal to the transponder at 116 and, depending on which mode was originally selected by the user at step 102, may select either record or analyze mode at 122. If the analyzer goes into analyze mode, it loads at 124 the waveform data obtained while in record mode during a prior first period of time and loads at 126 the waveform data obtained while it is in its present analyze mode. It then analyzes the data to determine the difference between the waveforms at 128. (Step 126 can precede step 124). The analyzer at 130 compares that difference to a "threshold" value and at 131 determines if that difference is greater than the threshold. If the difference between the waveforms is greater than the threshold, the analyzer displays a constriction alert at 132 and ends its data analysis at 134. On the other hand, if the analyzer determines at 130 that the difference in the waveforms is less than the threshold it will end its analysis at 134 without displaying a constriction alert. If the analyzer at 122 proceeds in response to a selection at 102 of record mode, it will proceed directly to step 134 from step 122 without any intervening data analysis.

Regarding the transponder, the sequence is as follows: The transponder receives a signal from the analyzer at 200 and then determines at 202 whether it was a start scan or an end scan signal. If it received a start scan signal, the transponder proceeds to activate the Hall Effect transducer, the instrumentation amplifier, the voltage to frequency converter and the signal transmitter at 204. The Hall Effect transducer receives a signal from the magnetic composition at 206, which signal is amplified at 208, converted to a frequency signal at 210, and transmitted as a frequency-modulated signal to the analyzer at 212. The transponder continues in scan mode until it receives an end scan signal at 200. In response to the detection of an end scan signal at 202, the transponder deactivates the Hall Effect transducer, the amplifier, the converter and the transmitter at 214. That results in the scan being completed at 216.

The invention can be used to measure flow through conduits of relatively small cross sectional area, for example those with diameters in the range 2.5 to 5 cm. The magnetic composition, especially if it is in the form of a paste that is spread over a portion of the outer surface of the conduit, does not appreciably alter the diameter of the conduit.

The signal transmitters (35,65) of the transponder and signal analyzer preferably send FM signals, the signals being transmitted at frequencies selected for their ability to pass through the skin barrier and not disrupt neighboring devices, such as a pacemaker. Absent consideration of pacemakers, preferred transmitted frequencies will be in a range from 165 kHz to 185 kHz.

The system components for fabrication of the circuits shown in FIG. 4 and 5 are commercially available from sources such as Honeywell, Analog Devices, and Radio Shack. In order to construct the transponder circuit of FIG. 4 with sufficiently small dimensions (e.g., within a disk-shaped housing having a diameter of about 1 cm and a thickness of about 0.5 cm) current available chip technology can be used.

The implanted prosthetic 15 can be of commercially available materials, for example, Gore-Tex or Dacron, that is coated with a magnetic composition that can be produced and applied using the following process. Commercially available small magnets are crushed into very fine particles. A nontoxic bonding agent is applied to the conduit over the area of interest. The fine magnetic particles are uniformly dispersed over the area of interest by temporarily placing a magnet inside the conduit to induce the fine magnetic particles to adopt the same magnetic field orientation. A thin bonding or sealing material of suitable flexibility is preferably over the area of interest to keep the magnetic particles from accidentally entering the body.

We claim:

1. A apparatus for measuring hemodynamic parameters related to blood flow comprising:

a surgically implantable expandable prosthetic conduit adapted to be in the limb of a human;

a magnetic composition, wherein the magnetic composition is a particle-epoxy composition that is coated around said surgically implanted expandable prosthetic conduit;

said magnetic composition affixed to said surgically implantable expandable prosthetic conduit which conduit is adapted to expand in response to fluctuations in fluid movement through the surgically implantable expandable conduit, and said conduit having a means for generating magnetic fluctuations;

a transponding means for receiving said magnetic fluctuations from said magnetic composition and emits voltage signals representative of the fluctuations;

a signal analyzer that receives the emitted signals, calculates a difference between signals and outputs associated electrical values indicative of blood flow.

2. The apparatus of claim 1, which includes means for receiving and displaying outputs from said associated electrical values.

3. The apparatus of claim 1, wherein the transponding means comprises a Hall Effect transducer.

4. A method for measuring hemodynamic parameters related to blood flow comprising:

providing a surgically implanted expandable prosthetic conduit in the limb of a human, for receipt of blood flow therethrough;

providing the conduit with means to generate a voltage indicative of blood flow;

measuring, at a distance from the conduit and over a first period of time, a voltage caused by the blood flow so as to generate a first waveform of voltage or current versus time;

measuring, at a distance from the conduit and over a second period of time, a voltage caused by the flow so as to generate a second waveform of voltage or current versus time;

calculating the difference between the first and second waveforms as to regards to their amplitudes or frequencies;

wherein the measuring steps each comprise the transmission of a wireless signal to a signal analyzer from a transponder affixed to the conduit, wherein the means to generate the voltage indicative of blood flow is generated by a Hall Effect transducer which is responsive to a flux of a magnetic composition affixed to the expandable conduit;

wherein the magnetic composition is a particle-epoxy composition that is coated around said surgically implanted expandable prosthetic conduit located in the limb of a human;

wherein the blood flow is pustile in nature and creates expansions in the surgically implanted expandable prosthetic conduit.

\* \* \* \* \*